(12) United States Patent
Shepard

(10) Patent No.: US 8,043,315 B2
(45) Date of Patent: Oct. 25, 2011

(54) OSTEOCHONDRAL REPAIR USING PLUG FASHIONED FROM PARTIAL DISTAL ALLOGRAFT FEMUR OR CONDYLE

(75) Inventor: David O. Shepard, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1943 days.

(21) Appl. No.: 10/947,217

(22) Filed: Sep. 23, 2004

(65) Prior Publication Data
US 2006/0060209 A1    Mar. 23, 2006

Related U.S. Application Data

(60) Provisional application No. 60/506,513, filed on Sep. 23, 2004.

(51) Int. Cl.
*A61B 17/32* (2006.01)
(52) U.S. Cl. ..................... 606/167; 623/16.11
(58) Field of Classification Search .............. 606/84, 606/86, 96, 86 R, 167, 88–89; 623/11.11, 623/16.11, 23.51, 23.61, 23.72, 23.75, 902, 623/908, 20.35, 18.11
See application file for complete search history.

(56) References Cited

U.S. PATENT DOCUMENTS

| | | | | |
|---|---|---|---|---|
| 5,616,146 A | * | 4/1997 | Murray | 606/80 |
| 5,919,196 A | * | 7/1999 | Bobic et al. | 606/86 R |
| 6,077,987 A | * | 6/2000 | Breitbart et al. | 623/23.72 |
| 6,146,385 A | * | 11/2000 | Torrie et al. | 606/96 |
| 6,231,608 B1 | * | 5/2001 | Stone | 623/16.11 |
| 6,443,987 B1 | * | 9/2002 | Bryan | 623/17.11 |
| 6,488,033 B1 | * | 12/2002 | Cerundolo | 128/898 |
| 6,500,206 B1 | * | 12/2002 | Bryan | 623/17.16 |
| 6,591,581 B2 | * | 7/2003 | Schmieding | 53/396 |
| 6,592,588 B1 | | 7/2003 | Bobic et al. | |
| 2002/0045940 A1 | * | 4/2002 | Giannetti et al. | 623/11.11 |
| 2002/0049613 A1 | * | 4/2002 | Schmieding | 705/2 |
| 2002/0052606 A1 | * | 5/2002 | Bonutti | 606/88 |
| 2002/0082704 A1 | * | 6/2002 | Cerundolo | 623/20.35 |
| 2002/0087274 A1 | * | 7/2002 | Alexander et al. | 702/19 |
| 2002/0157676 A1 | * | 10/2002 | Schmieding | 128/898 |
| 2002/0177770 A1 | * | 11/2002 | Lang et al. | 600/410 |
| 2004/0097929 A1 | * | 5/2004 | Branch et al. | 606/61 |
| 2004/0167390 A1 | * | 8/2004 | Alexander et al. | 600/410 |
| 2004/0230303 A1 | * | 11/2004 | Gomes et al. | 623/16.11 |

OTHER PUBLICATIONS

"Allogenic transplantation of femoral condyle after traumatic injury." Herzmann K, Grass R, Barthel S, Zwipp H. Unfallchirurg. Jan. 2002;105(1):71-4.*
"Biomechanical and topographic considerations for autologous osteochondral grafting in the knee." Ahmad CS, Cohen ZA, Levine WN, Ateshian GA, Mow VC. Am J Sports Med. Mar.-Apr. 2001;29(2):201-6.*

* cited by examiner

*Primary Examiner* — Thomas C. Barrett
*Assistant Examiner* — Christian Sevilla
(74) *Attorney, Agent, or Firm* — Dickstein Shapiro LLP

(57) ABSTRACT

A method and apparatus for repairing isolated chondral defects using allograft implants. Lesions in articular tissue are corrected by forming a recipient socket in the tissue. A donor graft of a size corresponding to the recipient socket is harvested from a partial tissue specimen obtained from allograft material. The donor graft is implanted into the recipient socket.

14 Claims, 12 Drawing Sheets

Current Cut for Hemi-condyles 3 cut partial condyle (includes Trochlear Groove)

4 cut partial condyle

US 8,043,315 B2

OSTEOCHONDRAL REPAIR USING PLUG FASHIONED FROM PARTIAL DISTAL ALLOGRAFT FEMUR OR CONDYLE

The present application claims the benefit of U.S. Provisional Patent Application No. 60/506,513, filed Sep. 23, 2004, the entire disclosure of which is incorporated by reference herein. The present application is also related to U.S. application Ser. No. 10/638,489, filed Aug. 12, 2003, the disclosure of which is incorporated herein by reference.

BACKGROUND OF THE INVENTION

1. Field of the Invention

The present invention relates to the surgical treatment of isolated articular chondral defects and, more specifically, to methods and instruments for replacement of articular cartilage in the knee using grafts harvested from a partial distal allograft femur or condyle.

2. Description of the Related Art

Methods and apparatus for surgical treatment of isolated articular chondral defects by autograft and allograft transplantation are known. See, for example, U.S. Pat. Nos. 5,919,196, 6,591,581, and 6,592,588, having common assignment with the present application.

FIG. 1 illustrates a prior art procedure for obtaining an allograft hemi-condyle for use in an osteochondral repair procedure. A cadaveric distal femur 10 is cut into two hemi-condylar portions 12 and 14. Disadvantageously, harvesting of bone material from the allograft hemi-condyle leaves significant portions of the hemi-condyle as waste. In addition, hemi-condyles do not provide an intact trochlear region. Repair of defects in the trochlear region requires whole distal femurs, which results in further, significant tissue loss since residual condyles are discarded.

Cutting the distal femur into partial condyles would provide a more efficient use of the distal femur. Reducing the size of the partial condyles also facilitates processing of the allogeneic graft material. Processing of the allogeneic material is facilitated, for example, by increasing available surface area for graft cleaning, and reducing blood and lipid residuals that may impact negatively the viability of chondrocytes, an important factor in procedure outcome.

Accordingly, it would be advantageous to provide a method and system for creating and utilizing partial allograft femurs or condyles in the repair of isolated chondral defects.

SUMMARY OF THE INVENTION

The present invention provides methods and apparatus for repair of isolated chondral defects using partial allograft distal femurs or condyles. The procedure can be utilized, for example, to anatomically reestablish a structural load-bearing surface to a damaged load bearing surface of a patient's femoral condyle. Osteochondral implants used in the procedure are harvested from partial allograft specimens. Partial and full-thickness osteochondral lesions, 1.5-3.5 centimeters in diameter, are particularly amenable to treatment according to the methods of the present invention.

DETAILED DESCRIPTION OF THE PREFERRED EMBODIMENTS

In the present invention, a partial tissue specimen, such as a three-cut partial condyle, or a four-cut partial condyle, is obtained from allograft material, as described in greater detail below. The partial condyle is delivered to a surgeon, along with a set of surgical socket-forming and donor graft harvesting instrumentation. Based on a pre-operative assessment, the tissue specimen is obtained so as to provide material sufficient for the surgeon to harvest an appropriately sized plug for performing the indicated repair.

In addition, the specimen is selected to provide an articular surface that closely approximates that of the anatomical tissue being repaired. The surgeon uses the instrumentation provided to fashion a donor graft, or plug, from the partial tissue specimen. The plug is used for osteochondral repair of the damaged articular surface. The procedure is described below, with reference to the accompanying drawings.

Figure 1:
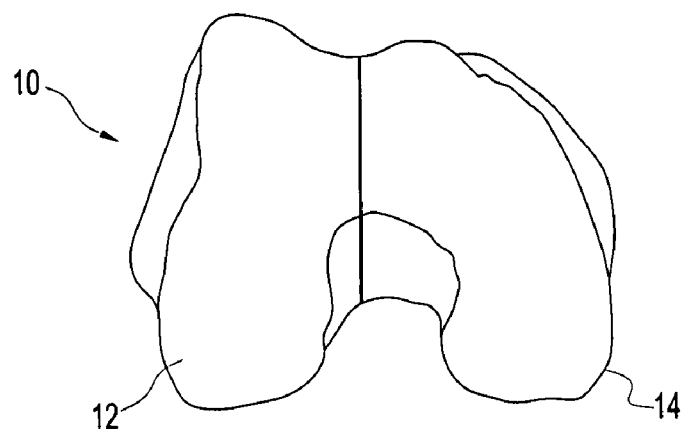
FIG. 1 illustrates a prior art method of obtaining hemi-condyles from an allograft distal femur.
Figure 2:
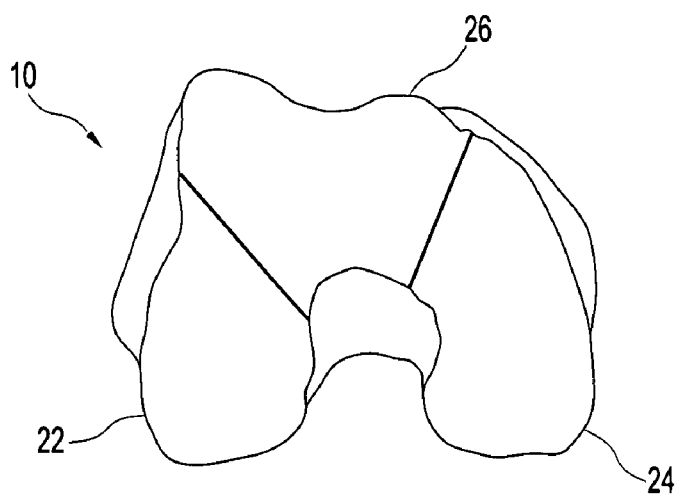
FIG. 2 illustrates a method of obtaining three-cut partial condyles from an allograft distal femur in accordance with the present invention.
Figure 3:
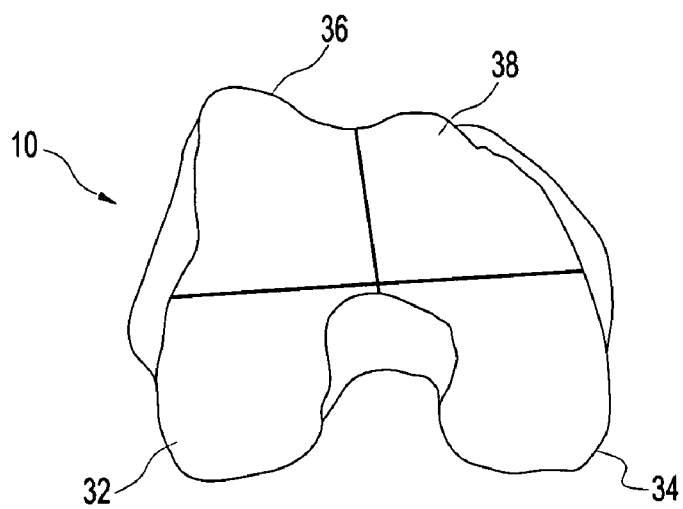
FIG. 3 illustrates a method of obtaining four-cut partial condyles from an allograft distal femur in accordance with the present invention.

Referring to FIGS. 2 and 3, partial allograft tissue specimens are obtained by cutting distal femur 20 into sections. As shown in FIG. 2, three-cut partial condyles 22 and 24 are obtained by cutting the distal femur 10 into three sections to achieve a lateral condylar portion 22, a medial condylar portion 24, and a trochlear portion 26. FIG. 3 illustrates a four-cut procedure in which four portions are achieved from distal femur 10, including lateral and medial condylar portions 32 and 34, and two trochlear portions 36 and 38. The condylar portions obtained by the four-cut procedure generally are smaller than those obtained by the three-cut procedure.

After the cutting procedure, the portions are measured for adequacy of core yield. Referring to FIG. 2, the two partial condyles 22, 24 each are sized by measuring a width lateral to medial and a length anterior to posterior of the remaining articular surface. A 20 mm sizing dowel is used to confirm that at least one single 20 mm diameter core may be obtained from each partial. Additional sizing dowels may be used if the graft is able to yield additional or larger cores. All measurements and core yield determinations are recorded.

The portion 26 including the trochlear groove also is sized to confirm adequate yield. The processed donor trochlear grooves are sized by measuring a width across the patellar surface from the cut of one lateral groove to the cut made at the medial groove. A length measurement is taken from the bottom of the groove to the top of the cartilage. Finally, a depth measurement is taken by placing a straightedge across the patellar surface at midlevel and measuring the depth at the deepest point. All measurements and core yield determinations are recorded.

Referring to FIG. 3, 4-cut partials condyles 32, 34, 36, 38 are sized by measuring the width lateral to medial and the length anterior to posterior of the remaining articular surface of each partial. A 15 mm sizing dowel is used to assure that at least one single 15 mm core may be obtained from the graft. Additional sizing dowels may be used if the graft is capable of yielding additional or larger cores. All measurements and core yield determinations are recorded.

Condylar portions thus obtained are sized to indicate the largest single plug that can be obtained from each. Preferably, at least a 15 or 20 mm plug can be harvested from each of the partial condyles. Selected partial condyles are sent upon request to surgeons to be used as partial allograft condyle in the surgical repair procedure described below.

Figure 4:
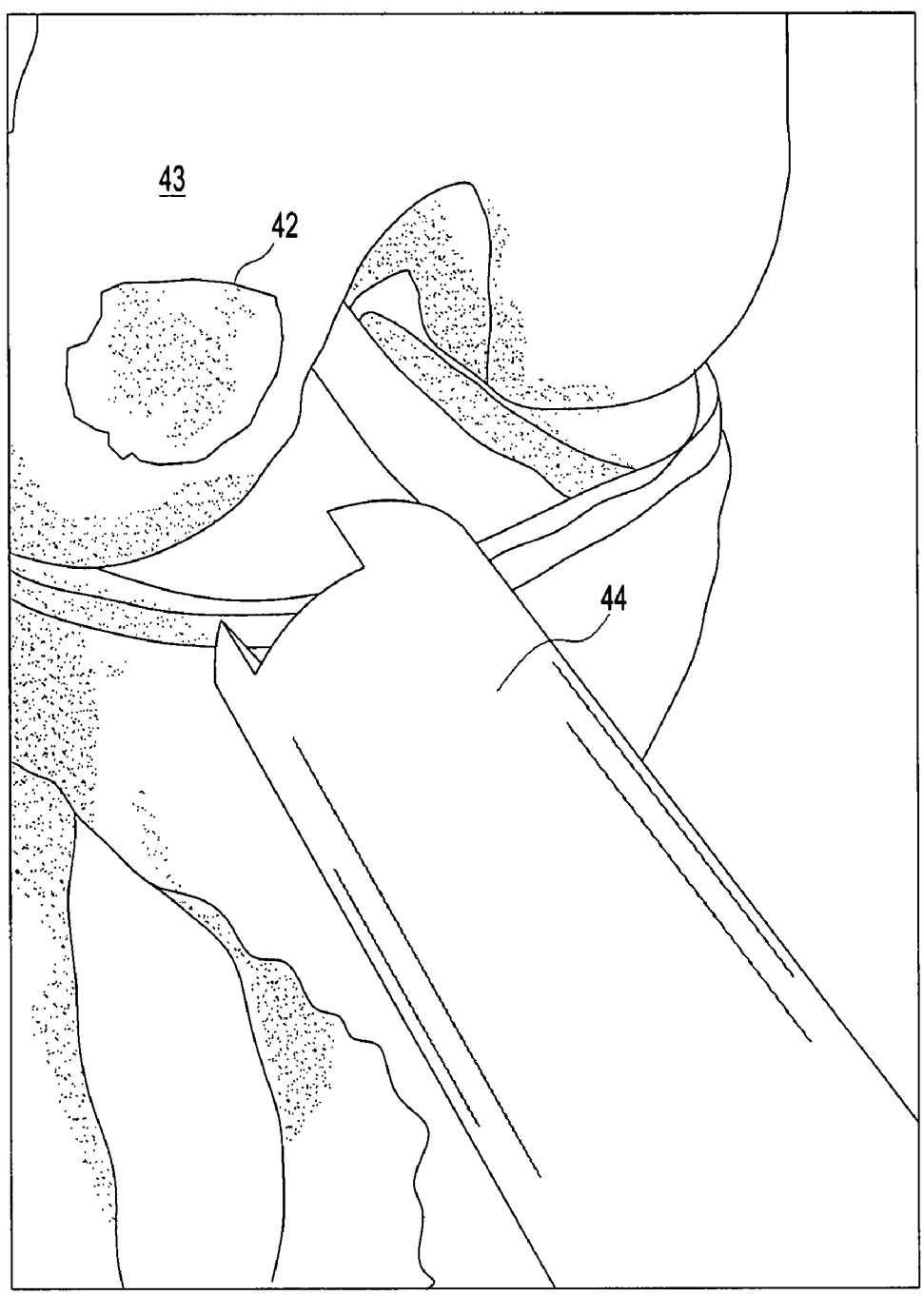
FIG. 4 illustrates a surgical step of sizing a lesion according to the present invention.

Referring to FIG. 4, the surgical procedure for osteochondral repair begins with standard pre-operative examination and diagnostic studies to confirm the size and extent of the lesion 42 on an articular surface of femoral condyle 43, a standard para-patellar arthrotomy is carried out to expose the defect. Cannulated sizers 44 in various diameters are selected to estimate and approximate coverage of the lesion 42. Sizers 44 preferably are provided in sizes of 12, 14, 15, 16, 18, 20, 25, 30, and 35 millimeter diameters, typically in various combinations.

Figures 5, 6:
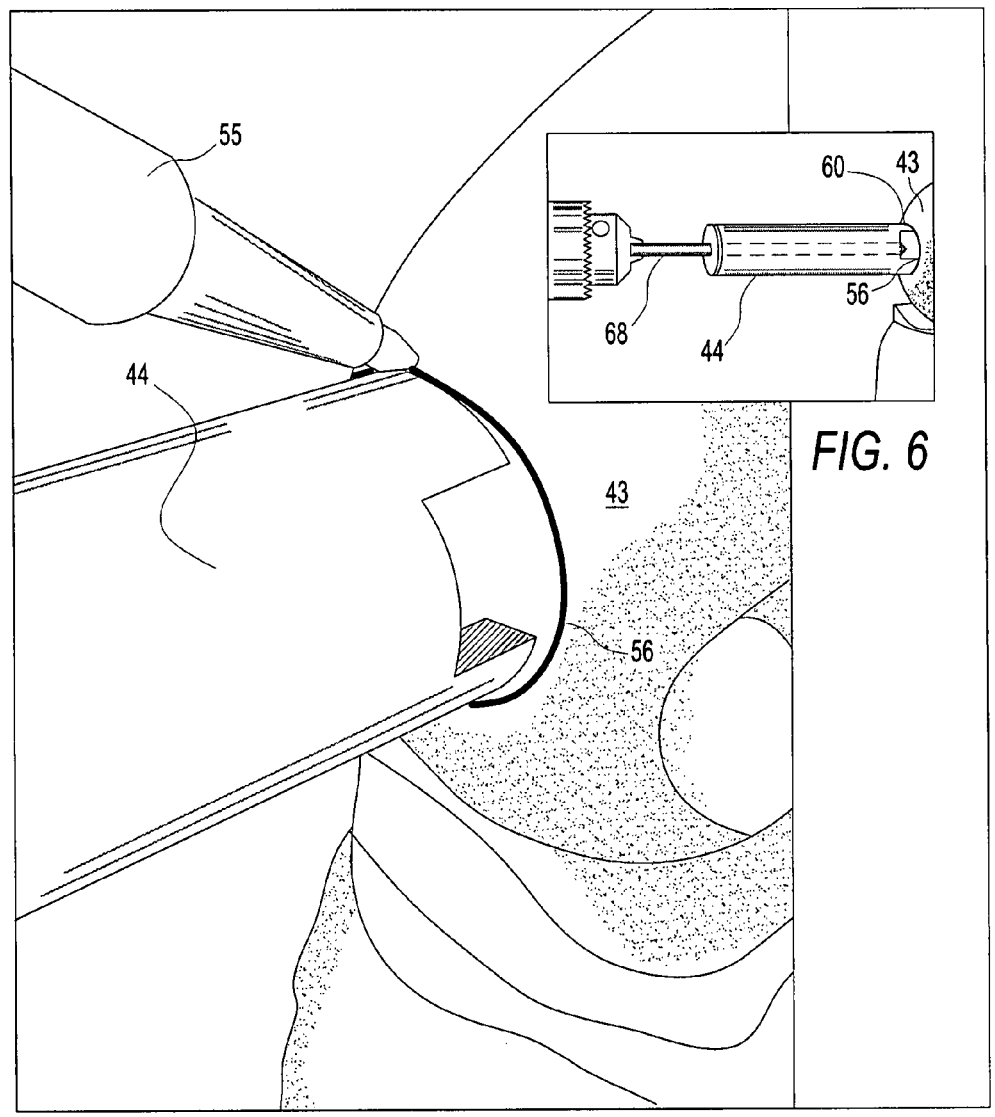
FIG. 5 illustrates a surgical step of marking an articular surface according to the present invention.
FIG. 6 illustrates a surgical step of drilling a guide pin into bone according to the present invention.

Referring to FIG. 5, once the appropriate size for the recipient socket is determined, a marker 55 is used to form a circumferential mark 56 on the damaged condyle 43 around the cylinder of sizer 44. As shown in FIG. 6, a guide pin 68 is drilled through the sizer 44 past the lesion 42 and into bone. The sizer 44 is removed and a reference mark 60 is placed in a superior 12:00 o'clock position.

Figures 7, 8:
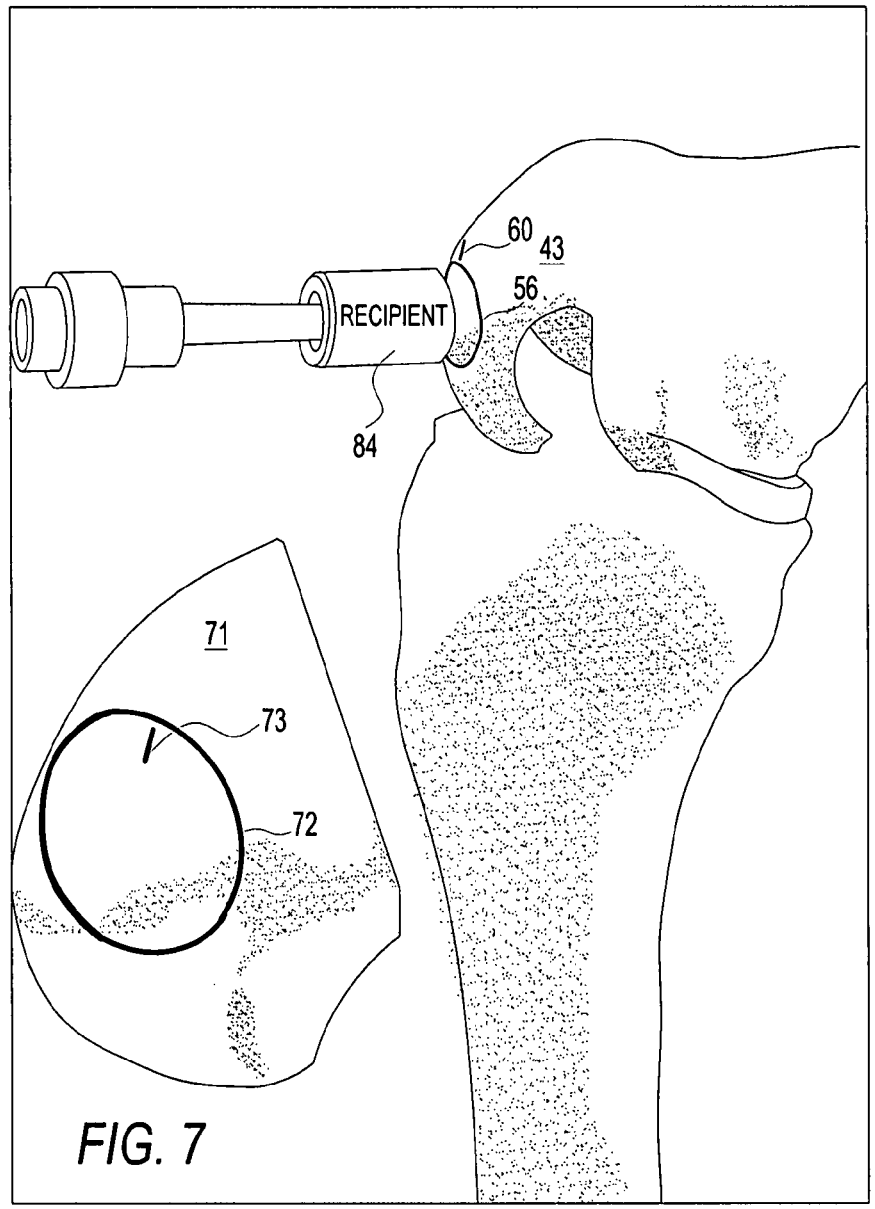
FIG. 7 illustrates a surgical step of marking a partial allograft condyle according to the present invention.
FIG. 8 illustrates a surgical step of scoring peripheral cartilage according to the present invention.

Referring to FIG. 7, markings are placed on a partial allograft condyle 71 using the sizer 44 which was previously utilized to establish the recipient defect size and mark the damaged condyle 43. A method of obtaining the partial condyle 71 is described above. The sizer 44 is placed over the partial allograft condyle 71 and is used to circumferentially mark 72 the surface of the partial allograft 71 in an area corresponding to that of the lesion 42 on the damaged articular surface of condyle 43. The sizer is removed and a reference mark 73 is placed in a superior 12:00 o'clock position on the inside of the circle mark 72 on the partial allograft condyle 71.

Referring to FIG. 8, the sizer is replaced by an appropriately-sized recipient harvester 84. Peripheral cartilage surrounding the damaged condylar surface is scored to the underlying subchondral bone. Scoring the peripheral cartilage obviates ancillary damage to the undamaged, peripheral articular surface. The harvester 84 is removed, leaving the guide pin 68 in place.

Figure 9:
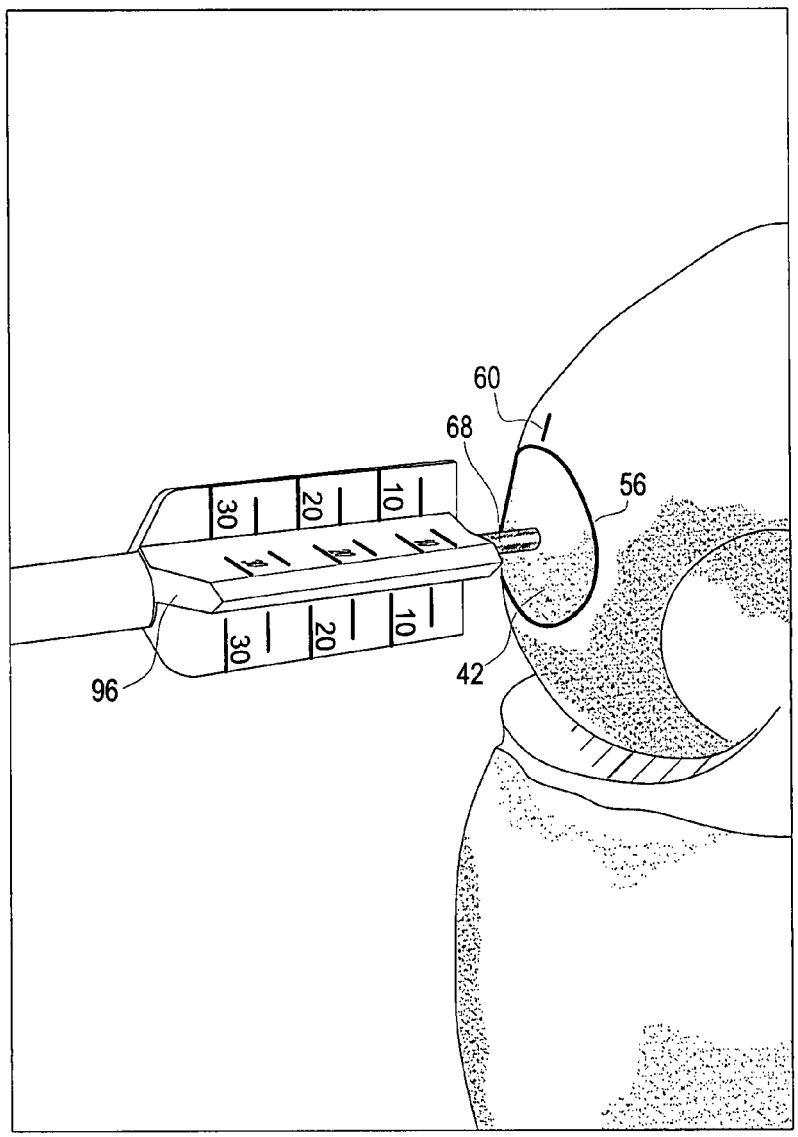
FIG. 9 illustrates a surgical step of boring into bone to form a recipient socket site according to the present invention.

Referring to FIG. 9, a cannulated calibrated recipient counterbore 96 is secured to the drill and placed over the drill pin 68. Recipient socket 97 (FIG. 12) is drilled into the lesion 42 and subchondral bone to a depth of 8 to 10 mm. Bleeding subchondral surfaces should be confirmed.

Figure 10:
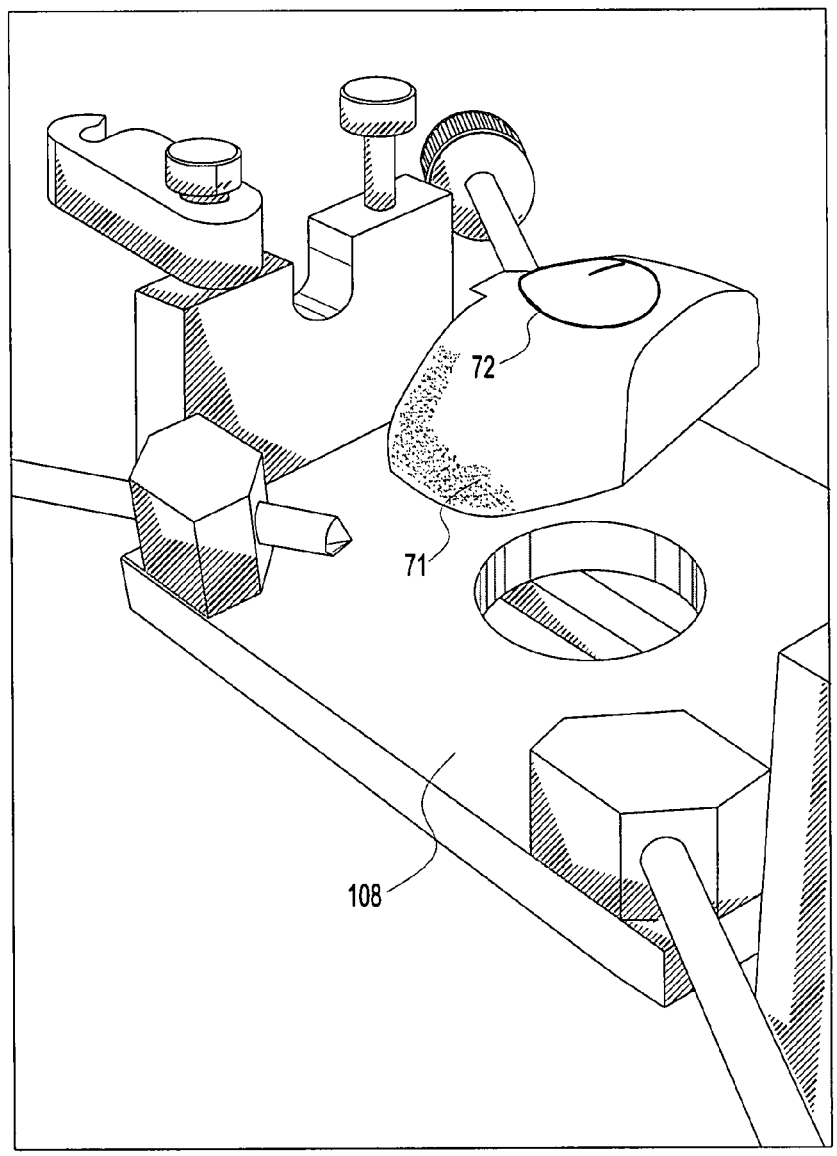
FIG. 10 illustrates a surgical step of securing the partial allograft condyle in a workstation according to the present invention.
Figure 11:
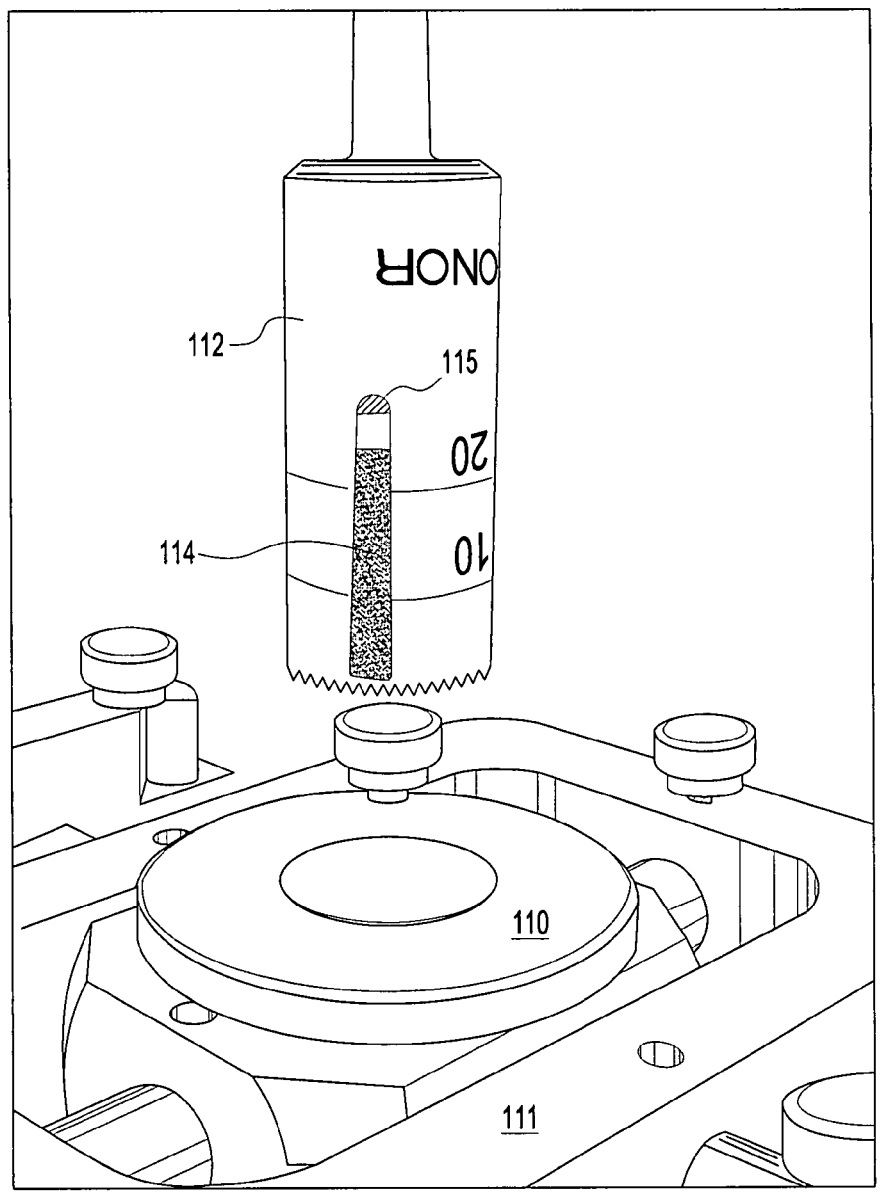
FIG. 11 illustrates a surgical step of harvesting a core from the partial allograft condyle secured in the workstation according to the present invention.

Preparation of the donor graft is described with reference to FIGS. 10-13. Referring to FIG. 10, donor partial condyle 71 is secured in a workstation 108. As shown in FIG. 11, a workstation bushing 110 of corresponding size is placed into a top housing 111 over the donor partial condyle 71 and set to the exact angle necessary to match the recipient's contour. The housing 111 is fastened securely.

A calibrated donor harvester 112 is connected to a drill and passed through the bushing 110 into the proximal graft housing 111 and rested upon the surface of the donor partial condyle 71. The harvester 112 is drilled through the entirety of the donor partial condyle 71. The harvester 112 is removed from the graft housing, securely holding the corresponding cylindrical donor graft core 114, which can be visualized through slot 115. Donor graft 114 is extracted gently from the harvester 112 so as not to disturb the articular surface or underlying subchondral bone.

Figure 12:
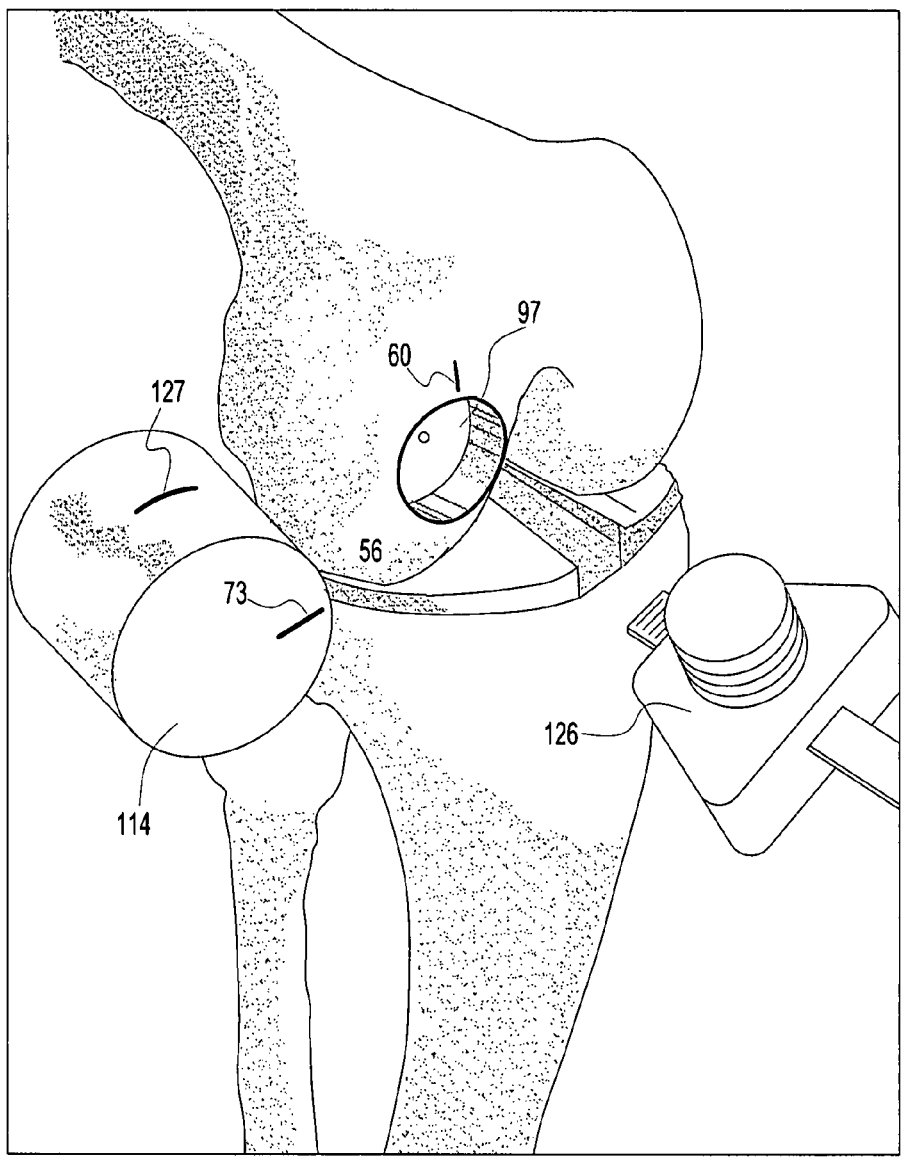
FIG. 12 illustrates a surgical step of transferring depth measurements to the core according to the present invention.

Referring to FIG. 12, a depth measurement guide 126 is used to measure the recipient depth in four quadrants: north, south, east, and west. The depth measurements are transferred to the allograft graft core 114, which is appropriately measured and marked 127 by referencing the four quadrant depths recorded from the recipient socket 97 that was created.

Figure 13:
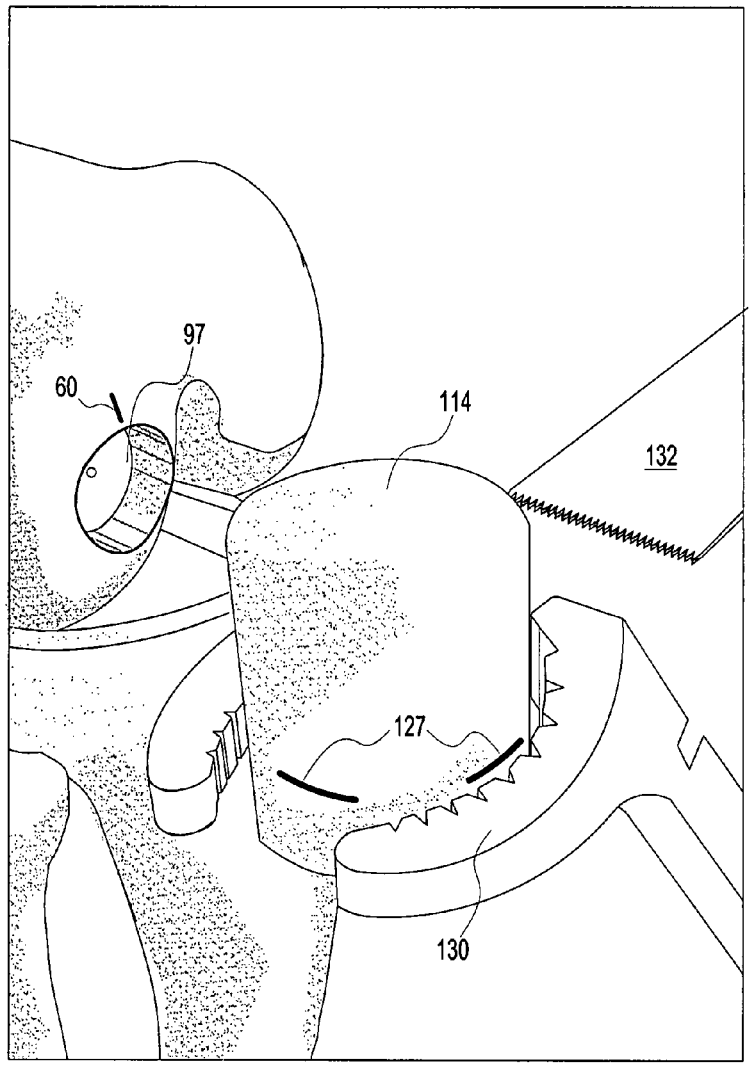
FIG. 13 illustrates a surgical step of cutting the harvested core to length according to the present invention.

Referring to FIG. 13, the donor graft 114 is secured in holding forceps 130 and trimmed by a reciprocating saw 132 to achieve the appropriate press fit accommodation of the recipient socket depth. The donor graft 114 is positioned with the articular surface inferior to cut.

Figure 14:
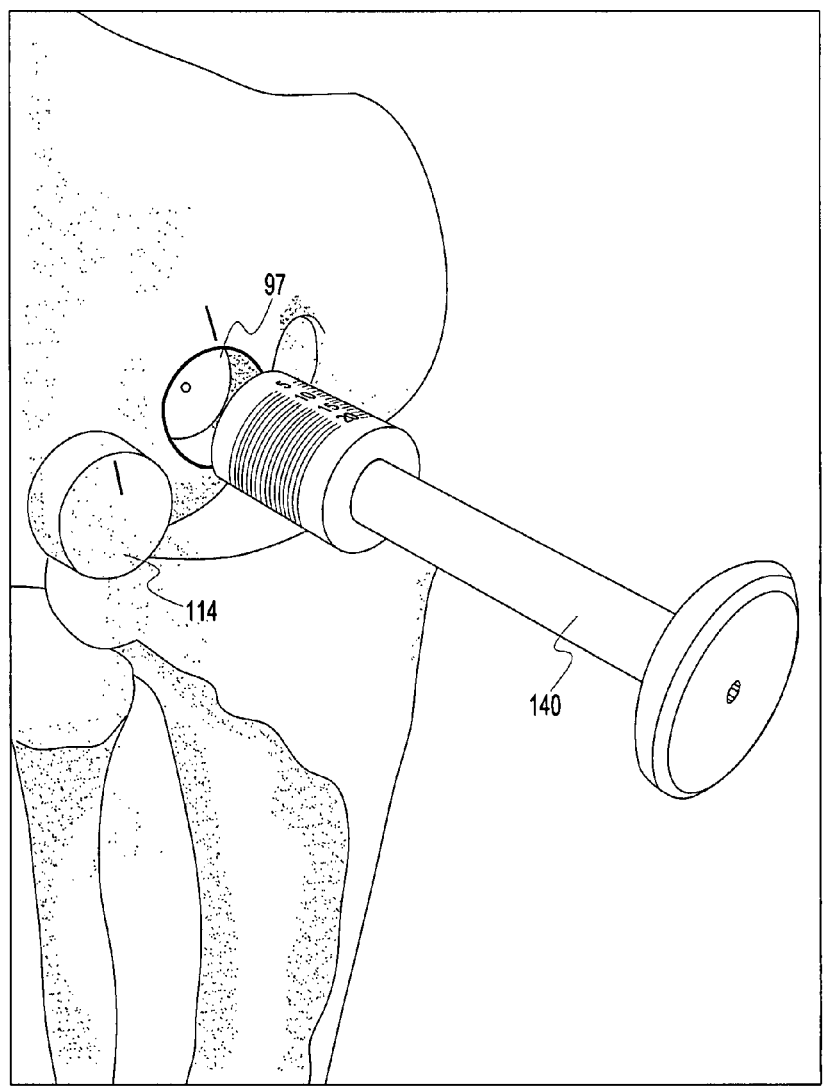
FIG. 14 illustrates a surgical step of dilating the recipient socket site according to the present invention.

Referring to FIG. 14, a calibrated dilator 140 is inserted into the recipient socket site 97 to achieve a one half mm socket dilation. The end of the dilator is tapped lightly with a mallet. Dilation also smooths the recipient socket surfaces.

Figure 15:
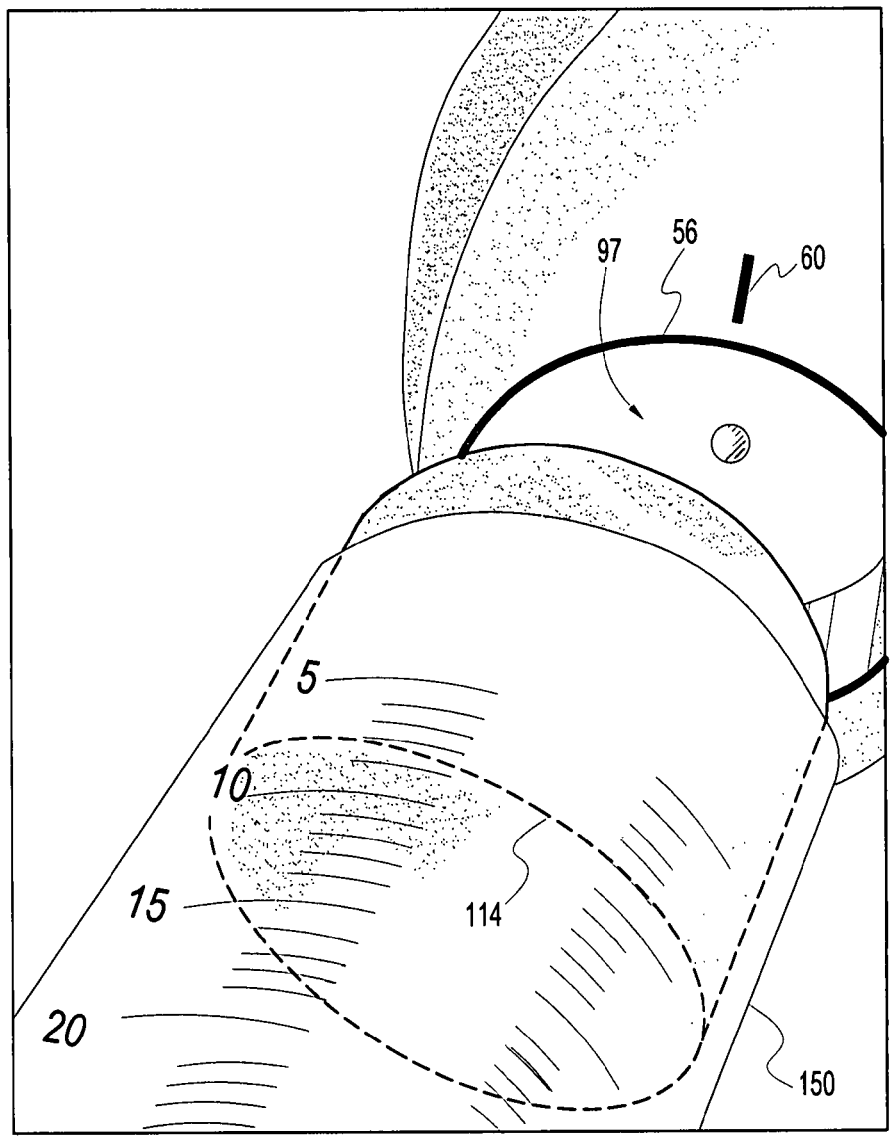
FIG. 15 illustrates a surgical step of placement of the harvested core into the recipient socket using a delivery tube according to the present invention.
Figure 16:
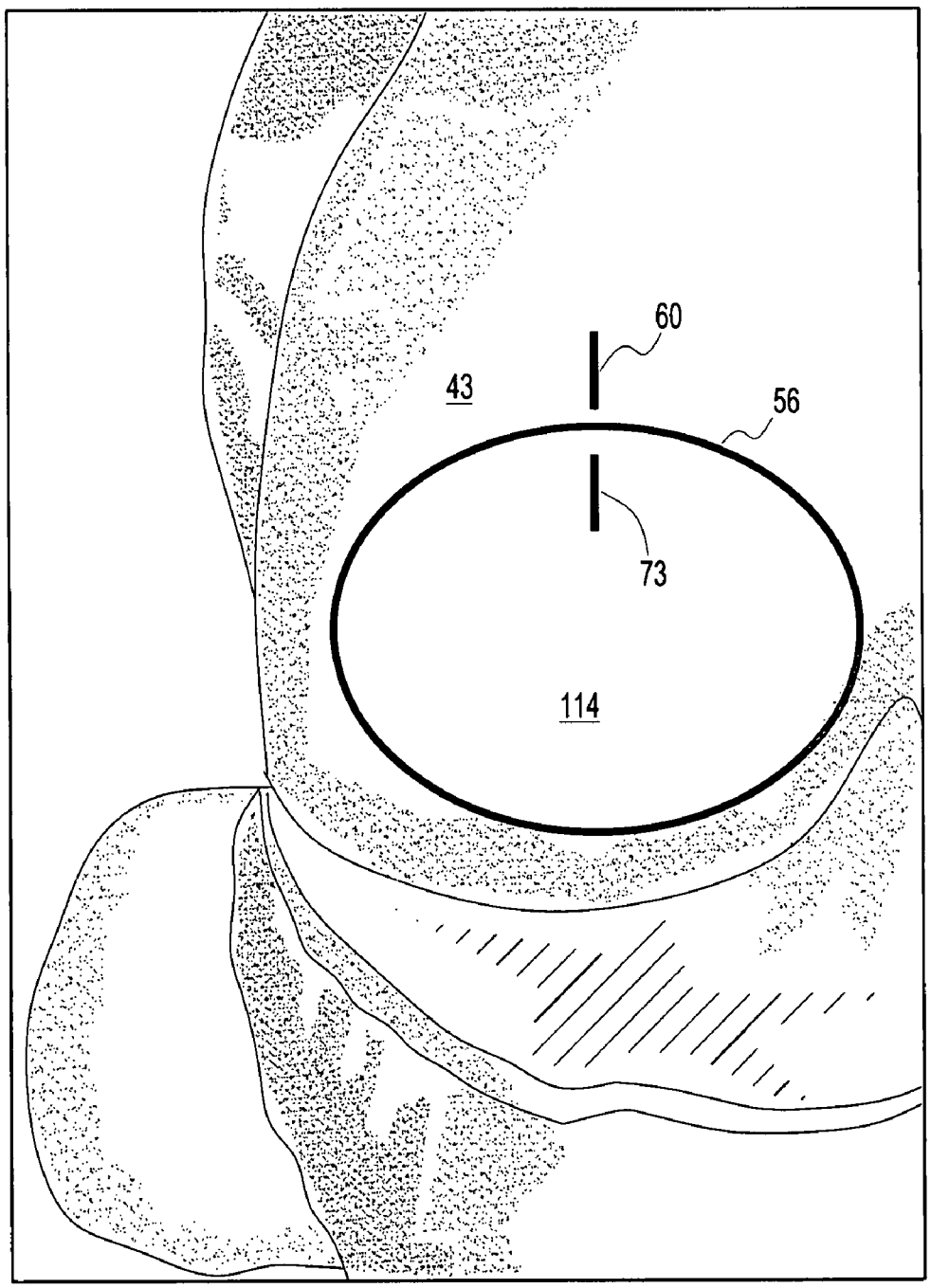
FIG. 16 illustrates a complete core implant according to the present invention.

Referring to FIG. 15, once the precise depth of the donor plug (matching the recipient socket) is obtained, the donor plug 114 is line to line fitted with reference to the marks 60 and 73 into the recipient socket. Cancellous graft is inserted into the bed prior to insertion of the donor plug, if necessary. The donor graft 114 is inserted into a slotted, transparent, calibrated delivery tube 150 for insertion into the recipient socket 97. A tamp corresponding to the graft's size is positioned against the plug. Gentle taps are recommended for seating the graft 114 into the socket 97. Referring to FIG. 16, the plug 114 is implanted until all edges are flush with the surrounding cartilage rim.

In situations necessary for plug removal, a graft retriever may be secured into the plug to facilitate extraction. At the conclusion of the procedure, the wound is closed in a routine fashion. Sterile dressing and a protective brace are applied during the initial wound-healing phase. Ambulation with the use of crutches and weight-bearing allowances are determined based on the size and the extent of the weight-bearing lesion reconstructed.

Although the present invention has been described in connection with preferred embodiments, many modifications and variations will become apparent to those skilled in the art.

What is claimed as new and desired to be protected by Letters Patent of the United States is:

1. A method of repairing isolated chondral defects, comprising:
   a first step comprising:
   forming a recipient socket in condylar tissue;
   providing a distal femur allograft specimen closely approximating the shape of the condylar tissue; and cutting the distal femur allograft specimen into three or four sections to obtain a partial distal femur allograft specimen formed as one of a three-cut partial or a four-cut partial; and a second step comprising:

harvesting a donor graft from the partial distal femur allograft specimen;

securing the partial distal femur allograft specimen in a workstation and cutting the donor graft from the partial distal femur allograft specimen using a harvester; and implanting the donor graft in the recipient socket;

and wherein the second step is performed after the first step.

2. A method according to claim 1, wherein the donor graft is harvested from the partial distal femur allograft specimen in the form of a plug corresponding in shape to the recipient socket formed in the condylar tissue.

3. A method according to claim 1, wherein the recipient socket is formed in an articular surface.

4. A method according to claim 3, wherein the socket is formed by scoring peripheral cartilage on the articular surface to underlying subchondral bone, and boring a counterbore in the subchondral bone.

5. A method according to claim 4, further comprising dilating the recipient socket.

6. A method according to claim 1, wherein the step of forming a recipient socket includes determining a size of a lesion to be repaired.

7. A method according to claim 6, further comprising marking the size of the lesion on a surface of the condylar anatomical tissue, and providing a reference mark on the surface.

8. A method according to claim 7, further comprising providing a corresponding reference mark on a surface of the donor graft.

9. A method according to claim 1, wherein implanting the donor graft in the recipient socket includes aligning reference marks formed at the recipient socket and on the donor graft, and impacting the donor graft into the recipient socket.

10. A method according to claim 1, further comprising cutting the donor graft to achieve a length equal to a depth of the recipient socket.

11. A method according to claim 1, the method comprising steps of:

cutting the distal femur allograft specimen into sections to achieve two condylar portions and at least one trochlear portion.

12. The method of claim 11, wherein the distal femur allograft specimen is cut into a lateral condylar portion, a medial condylar portion and one trochlear portion.

13. The method of claim 11, wherein the distal femur allograft specimen is cut into four sections to achieve two condylar portions and two trochlear portions.

14. The method of claim 11, further comprising the step of sizing the condylar portions to indicate the largest single plug that can be obtained from each condylar portion.

* * * * *